United States Patent
Amato et al.

(10) Patent No.: US 6,329,393 B1
(45) Date of Patent: Dec. 11, 2001

(54) CRYSTALLINE PHARMACEUTICALLY ACCEPTABLE SALTS OF AN OXAZOLIDINONE DERIVATIVE

(75) Inventors: Joseph S. Amato, Brooklyn; Zhen Li, Scotch Plains, both of NY (US); James A. McCauley, Belle Meade, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/460,267

(22) Filed: Dec. 13, 1999

Related U.S. Application Data

(60) Provisional application No. 60/112,757, filed on Dec. 17, 1998.

(51) Int. Cl.[7] .................. A61K 31/445; C07D 413/12
(52) U.S. Cl. ............................................. 514/326; 546/209
(58) Field of Search ............................. 514/326; 546/209

(56) References Cited

U.S. PATENT DOCUMENTS 3,816,612 * 6/1974 Schmit et al. ........................ 424/45
6,159,990 * 12/2000 Lagu et al. ........................... 514/326

FOREIGN PATENT DOCUMENTS

| | | |
|---|---|---|
| WO 96/14846 | 5/1996 | (WO). |
| WO 97/17969 | 5/1997 | (WO). |
| WO 97/42956 | 11/1997 | (WO). |
| WO 98/57940 | 12/1998 | (WO). |
| WO 99/48530 | 9/1999 | (WO). |

OTHER PUBLICATIONS

Berge et al. "Pharmaceutical Salts" J. Pharm. Sciences, v.66(1) p. 1–20 (1977).*

* cited by examiner

*Primary Examiner*—Celia Chang
(74) *Attorney, Agent, or Firm*—Baerbel R. Brown; Kenneth R. Walton; Melvin Winokur

(57) ABSTRACT

A crystalline pharmaceutically acceptable benzenesulfonate salt of Compound A of formula:

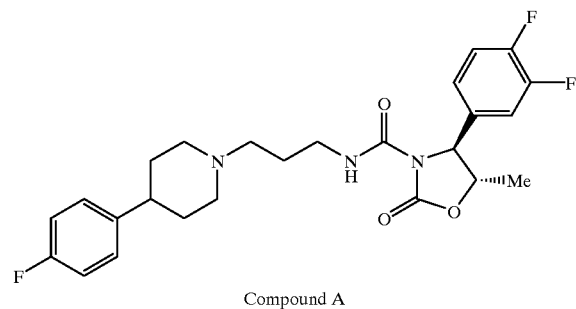

Compound A and solvates thereof are disclosed. Compound A and its benzenesulfonate salts are alpha 1a adrenergic receptor antagonists useful in the treatment of benign prostatic hyperplasia. Pharmaceutical compositions employing the crystalline salts, and processes for making and using the crystalline salts are also disclosed.

20 Claims, No Drawings

CRYSTALLINE PHARMACEUTICALLY ACCEPTABLE SALTS OF AN OXAZOLIDINONE DERIVATIVE

This application claims the benefit of U.S. Provisional Application No. 60/112,757, filed Dec. 17, 1998.

FIELD OF THE INVENTION

The present invention relates to crystalline pharmaceutically acceptable salts of an oxazolidinone derivative which is useful as an alpha 1a adrenergic receptor antagonist. More specifically, the invention provides a crystalline pharmaceutically acceptable, benzensulfonic acid salt of Compound A (defined below), pharmaceutical compositions employing the crystalline salt, and processes for making and using the crystalline salt.

BACKGROUND OF THE INVENTION

Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concomitantly, the increased noradrenergic innervation of the enlarged prostate leads to an increased adrenergic tone of the bladder neck and urethra, further restricting the flow of urine through the urethra.

Recent advances in molecular biology have identified the alpha 1a adrenoceptor subtype as the predominant alpha 1 receptor that mediates the contraction of prostate and lower urinary tract smooth muscle. Several classes of compounds have been disclosed to be selective alpha 1a adrenergic receptor antagonists useful for treating BPH. For example, WO 96/14846, WO 97/17969 and WO 97/42956 each disclose certain dihydropyrimidine derivatives (e.g., certain 1,2,3,6-tetrahydro-2-oxo-pyrimidine derivatives) which are selective antagonists for the human alpha 1a receptor and useful for treatment of BPH, impotency, cardiac arrhythmia, and other diseases where antagonism of the alpha 1a receptor may be useful.

Compound A is a potent and selective antagonist of the alpha 1a adrenergic receptor antagonist and is useful in the treatment of BPH. More particularly, the compound is (4S,5S)-4-(3,4-difluorophenyl)-N-[3-[4-(4-fluorophenyl)-1-piperidinyl]propyl]-5-methyl-2-oxo-3-oxazolidine carboxamide and has the formula:

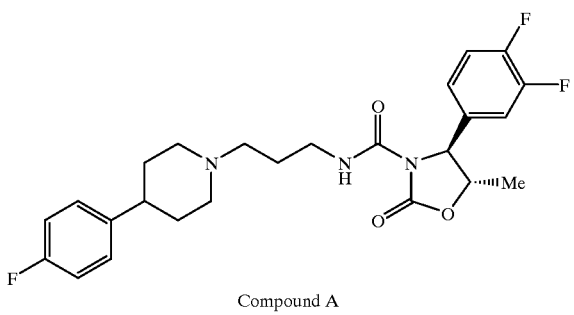

Compound A

Because free base Compound A can be sensitive to bases and, with the nitrogen atom not being protonated, can also be susceptible to oxidation, a pharmaceutically acceptable salt of Compound A is desirable. Preparation of an acceptable salt of Compound A suitable for pharmaceutical development has been problematic. Numerous attempts to isolate a crystalline salt formn of Compound A failed as only amorphous salts could be isolated. A crystalline salt which was isolated had too low a melting point to be practical for processing into pharmaceutical compositions.

These problems were solved by identification of the crystalline pharmaceutically acceptable benzenesulfonic acid salt of Compound A of the present invention.

SUMMARY OF THE INVENTION

The present invention provides a crystalline pharmaceutically acceptable salt, which is the benzenesulfonic acid salt of Compound A of Formula (I):

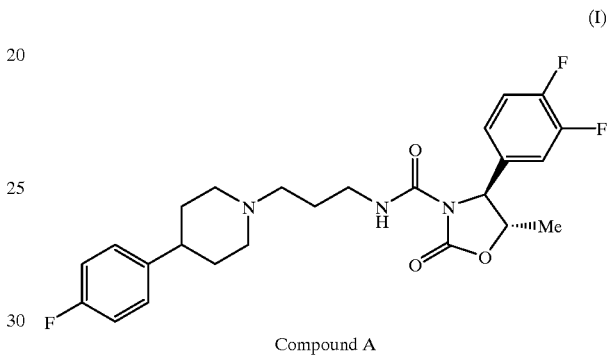

Compound A or a solvate thereof.

In one embodiment of the invention is the crystalline benzensulfonic acid salt of Compound A of Formula (II)

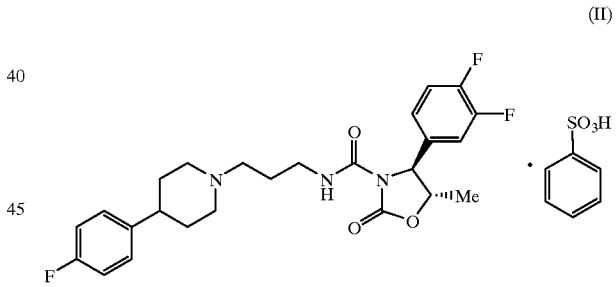

or a solvate thereof.

In another embodiment of the invention is a crystalline salt of Compound A characterized by a differential scanning calorimetry (DSC) curve at a heating rate of 10° C./min in an open cup under flowing nitrogen, exhibiting an endotherm with an extrapolated onset temperature of about 166° C., a peak temperature of about 168° C. and an associated heat of about 83 J/gm.

In still another embodiment of the invention is a crystalline salt of Compound A characterized by an x-ray powder diffraction pattern having d-spacings of 19.1, 13.3, 7.16, 6.87, 5.47, 5.05, 4.85, 4.70, 4.42, 4.10, 3.85, 3.62, 3.56, 3.38 and 3.14 Å.

The present invention includes a pharmaceutical composition comprising a crystalline benzenesulfonic acid salt of Compound A, or solvate thereof, and a pharmaceutically acceptable carrier. In one embodiment, the pharmaceutical composition further comprises a therapeutically effective amount of a testosterone 5-alpha reductase inhibitor. The testosterone 5-alpha reductase inhibitor can be a type 1, a type 2, both a type 1 and a type 2 (i.e., a three component combination comprising the crystalline salt as described above combined with both a type 1 testosterone 5-alpha reductase inhibitor and a type 2 testosterone 5-alpha reductase inhibitor) or a dual type 1 and type 2 testosterone 5-alpha reductase inhibitor. In an aspect of this embodiment, the testosterone 5-alpha reductase inhibitor is a type 2 testosterone 5-alpha reductase inhibitor. In another aspect, the testosterone 5-alpha reductase inhibitor is finasteride.

The invention also includes a pharmaceutical composition made by combining a crystalline benzenesulfonic acid salt of Compound A, or solvate thereof, and a pharmaceutically acceptable carrier, and optionally a testosterone 5-alpha reductase inhibitor as set forth in the preceding paragraph.

The present invention also includes a process for making a pharmaceutical composition comprising combining a crystalline benzenesulfonic acid salt of Compound A, or solvate thereof, and a pharmaceutically acceptable carrier.

The present invention further includes methods of treating benign prostatic hyperplasia, of inhibiting contraction of prostate tissue and of relaxing lower urinary tract tissue in a subject in need thereof which comprises administering to the subject a therapeutically effective amount of a crystalline benzenesulfonic acid salt of Compound A, or a solvate thereof, or pharmaceutical compositions described above. In one embodiment, the methods of treating BPH, of inhibiting contraction of prostate tissue and of relaxing lower urinary tract tissue in a subject in need thereof wherein the crystalline salt of Compound A, or solvate thereof, is administered in combination with a testosterone 5-alpha reductase inhibitor; e.g., finasteride.

The present invention also includes a process for making a crystalline pharmaceutically acceptable benzensulfonic acid salt of Compound A of formula:

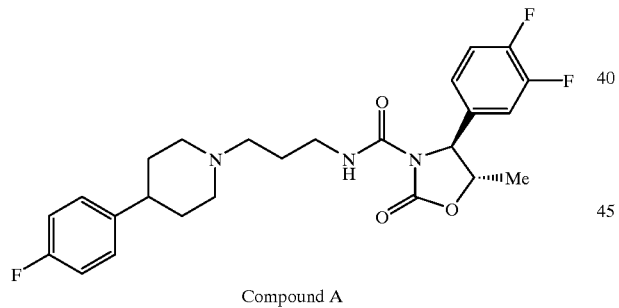

Compound A or a solvate thereof, which comprises:
(a) dissolving Compound A and benzensulfonic acid in a solvent to form a solution; and
(b) treating the solution of step (a) to form the crystalline salt.

In an embodiment of the process, at least about one mole equivalent of benzenesulfonic acid is dissolved in the solution per mole equivalent of Compound A.

In another embodiment of the process, dissolution step (a) comprises mixing Compound A in the solvent with the benzenesulfonic acid and then heating the mixture to form the solution. In an aspect of this embodiment, treatment step (b) comprises cooling the heated solution to form the crystalline salt.

In still another embodiment of the process, the solvent employed in dissolution step (a) is selected from methanol, ethanol, 2-propanol, ethyl acetate, isopropyl acetate, butanol, hexanes, toluene, ethyl ether, or a mixture thereof. A preferred solvent is ethanol.

In still another embodiment of the process, Compound A is dissolved in a solvent to form a (first) solution and benzenesulfonic acid is added thereto to form a final solution, which is treated to form the crystalline salt. In one aspect of this embodiment, the acid is added as a solution of the acid in a second solvent (which can be the same or different from the first solvent used to dissolve the free base of Compound A). The solvents set forth in the preceding paragraph are each independently suitable for use as the (first) solvent used to dissolve Compound A and the (second) solvent used to dissolve benzenesulfonic acid.

Exemplary of the invention is a process for forming a crystalline salt of formula:

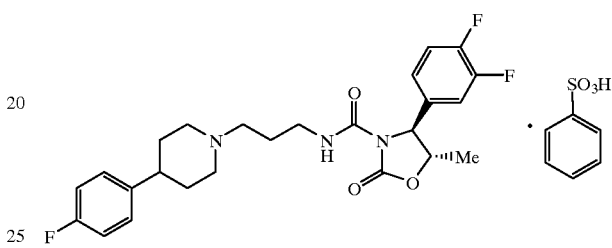

and solvates thereof, which comprises:
(a) heating a mixture of Compound A and benzensulfonic acid in ethanol to form a solution, wherein the mixture contains at least about one mole equivalent of benzensulfonic acid per mole equivalent of Compound A; and
(b) cooling the solution to form the crystalline salt.

A further exemplification of the invention is a crystalline pharmaceutically acceptable salt of benzenesulfonic acid, or a solvate thereof, made by dissolving a free base compound of formula:

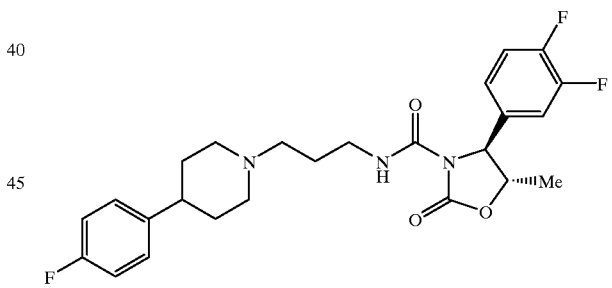

and benzenesulfonic acid in a solvent to form a solution; and treating the solution to form the crystalline salt.

An additional example of the invention is the use of the crystalline pharmaceutically acceptable benzenesulfonic acid salt of Compound A, or a solvate thereof, described above in the preparation of a medicament for: a) the treatment of benign prostatic hyperplasia; b) relaxing lower urinary tract tissue; or c) inhibiting contraction of prostate tissue; in a subject in need thereof.

Another illustration of the invention is the use of the crystalline pharmaceutically acceptable benzenesulfonic acid salt of Compound A, or a solvate thereof, described above and a 5-alpha reductase inhibitor for the manufacture of a medicament for: a) treating benign prostatic hyperplasia; b) relaxing urethral smooth muscle; or c) inhibiting contraction of prostate tissue which comprises an effective amount of the alpha 1a antagonist compound and an effective amount of 5-alpha reductase inhibitor, together or separately. In one embodiment, the 5-alpha reductase inhibitor is finasteride.

DETAILED DESCRIPTION OF THE INVENTION

The present invention provides a crystalline pharmaceutically acceptable salt, or a solvate thereof, of the potent and selective alpha 1a adrenergic receptor antagonist, Compound A, pharmaceutical compositions containing the salt, and methods of making and using the salt. The crystalline pharmaceutically acceptable salt of Compound A and pharmaceutical compositions of the present invention are useful in eliciting an alpha 1a antagonizing effect, in the prevention and/or treatment of BPH, and in relaxing lower urinary tract tissue.

The crystalline pharmaceutically acceptable benzenesulfonic acid salt of Compound A and pharmaceutical compositions thereof exhibit high selectivity for the human alpha 1a adrenergic receptor. One implication of this selectivity is that the salt displays selectivity for lowering intraurethral pressure without substantially affecting diastolic blood pressure.

The term "selective alpha 1a adrenergic receptor antagonist," as used herein, refers to an alpha 1a antagonist compound which is at least ten fold selective for the human alpha 1a adrenergic receptor as compared to the human alpha 1b, alpha 1d, alpha 2a, alpha 2b and alpha 2c adrenergic receptors.

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention also provides pharmaceutical compositions comprising the crystalline pharmaceutically acceptable salt of Compound A, or a solvate thereof, in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a crystaline salt of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" is intended to encompass a product comprising the specified ingredients in the specified amounts, as well as any product which results, directly or indirectly, from combination of the specified ingredients in the specified amounts.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The invention involves the formation of a crystalline pharmaceutically acceptable benzenesulfonic acid salt of the alpha 1a adrenergic receptor antagonist, Compound A, by (a) dissolving Compound A and benzenesulfonic acid in a solvent to form a solution; and (b) treating the solution of step (a) to form the crystalline salt. The free base of Compound A and benzenesulfonic acid can be mixed with a solvent and dissolved therein by heating the solution to a temperature in the range of from about room temperature to about 80° C. (e.g., from about 55 to about 75° C.). Typically at least about one mole equivalent of benzenesulfonic acid acid is employed per mole equivalent of Compound A (e.g., from about 1 to about 2 mole equivalents of acid per mole equivalent of Compound A). Preferably, equimolar amounts of Compound A and benzenesulfonic acid are employed.

In the dissolution step of the processes of making the crystalline pharmaceutically acceptable salt of the instant invention, Compound A and benzenesulfonic acid can be added to the solvent concurrently or sequentially in either order and the resulting mixture heated and/or stirred to form a solution. Alternatively, Compound A can be dissolved in the solvent to form a first solution, followed by the addition and dissolution therein of benzenesulfonic acid. Another alternative is to dissolve benzenesulfonic acid in a solvent, followed by addition and dissolution therein of Compound A. Still another alternative is to dissolve Compound A in a first solvent and benzenesulfonic acid in a second solvent (which may be the same or different from the first) and then mix the two solutions to form the salt solution.

A wide variety of solvents can be utilized as long as the Compound A free base is soluble in the solvent. Similarly, when the acid is added as a solution of the acid in a solvent, a wide variety of solvents can be used. Thus, suitable solvents for dissolving Compound A free base and/or the acid include, but are not limited to, water or esters, ketones, amides, ethers, alcohols and hydrocarbons, or mixtures thereof. Preferably, esters (e.g., ethyl acetate, isopropyl acetate), alcohols (e.g., methanol, ethanol, 2-propanol, butanol), hydrocarbons (e.g., hexanes, toluene) or mixtures thereof, are used as the solvent; more preferably, alcohols; most preferably, ethanol.

Thus, one aspect of the invention involves the formation of a crystalline pharmaceutically acceptable benzenesulfonic acid salt of the alpha 1a adrenergic receptor antagonist, Compound A, by dissolving the free base and benzenesulfonic acid in ethanol at a temperature of from about about 50 to about 80° C. followed by crystallization.

The crystalline salt and pharmaceutical compositions of the present invention are useful in eliciting an alpha 1a antagonizing effect. Thus, the crystalline salt and pharmaceutical compositions of this invention are useful in the prevention and/or treatment of BPH and for relaxing lower urinary tract tissue.

For these purposes, the crystalline salt of the present invention may be administered orally, parenterally (including subcutaneous injections, intravenous, intramuscular, intrastemal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating BPH and for relaxing lower urinary tract tissue. The treatment involves administering to a patient in need of such treatment a crystalline pharmaceutically acceptable benzenesulfonic acid salt of Compound A, or a solvate thereof; or a pharmaceutical composition comprising a pharmaceutical carrier and a therapeutically effective amount of a crystalline pharmaceutically acceptable benzenesulfonic acid salt of Compound A of the present invention, or a solvate thereof.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Compounds of this invention may be administered in any of the foregoing compositions and according to dosage regimens established in the art whenever specific blockade of the human alpha 1a adrenergic receptor is required.

The daily dosage of the products may be varied over a wide range from 0.01 to 1,000 mg per adult human per day. For oral administration, the compositions are preferably provided in the form of tablets containing 0.01, 0.05, 0.1, 0.5, 1.0, 2.5, 5.0, 10.0, 15.0, 25.0, 40.0, 50.0, 100, 250 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to 10 mg/kg of body weight per day, and especially from about 0.001 mg/kg to 7 mg/kg of body weight per day. The crystalline salt of Compound A may be administered on a regimen of 1 to 4 times per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The crystalline salt of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this includes administration of a crystalline salt of this invention and a human testosterone 5-α reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example). In addition to PROSCAR®, which is principally active in prostatic tissue due to its selectivity for human 5-α reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5α-reductase inhibitors have been described in WO93/23420, EP 0572166; WO 93/23050; WO93/23038,; WO93/23048; WO93/23041; WO93/23040; WO93/23039; WO93/23376; WO93/23419, EP 0572165; WO93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one preferred embodiment of the present invention, a method of treating BPH is provided which comprises administering to a subject in need of treatment a crystalline benzenesulfonic acid salt of the present invention in combination with finasteride effective to treat BPH. The dosage of finasteride administered to the subject is about 0.01 mg per subject per day to about 50 mg per subject per day in combination with an alpha 1a antagonist. Preferably, the dosage of finasteride in the combination is about 0.2 mg per subject per day to about 10 mg per subject per day, more preferably, about 1 to about 7 mg per subject to day, most preferably, about 5 mg per subject per day.

For the treatment of benign prostatic hyperplasia, the crystalline salt of this invention exhibiting alpha 1a adrenergic receptor blockade can be combined with a therapeutically effective amount of a 5α-reductase 2 inhibitor, such as finasteride, in addition to a 5α-reductase 1 inhibitor, such as 4,7β-dimethyl-4-aza-5α-cholestan-3-one, in a single oral, systemic, or parenteral pharmaceutical dosage formulation. Alternatively, a combined therapy can be employed wherein the alpha 1a adrenergic receptor antagonist and the 5α-reductase 1 or 2 inhibitor are administered in separate oral, systemic, or parenteral dosage formulations. See, e.g., U.S. Pat. Nos. 4,377,584 and 4,760,071 which describe dosages and formulations for 5α-reductase inhibitors.

Abbreviations used in the instant specification, particularly the Schemes and Examples, are as follows:

Ac=acetyl
DMF=N,N-dimethylformamide
EtOAc=ethyl acetate
HPLC=high performance liquid chromatography
LDA=lithium diisopropyl amide
Me=methyl
MeOH=methanol
MTBE=methyl tert-butyl ether
NMR=nuclear magnetic resonance
THF=tetrahydrofuran 4(S)-(3,4-difluorophenyl)-5(S)-methyloxazolidin-2-one precursor to Compound A can be prepared by treating 3,4-difluorophenylacetic acid with LDA, followed by reaction with acetaldehyde to form 2-(3,4-difluorophenyl)-3-methyl-3-hydroxypropionic acid, and then cyclizing the hydroxypropionic acid with diphenyldiphosphorylazide to form the oxazolidinone. The oxazolidinone can then be activated by treatment with p-nitrophenylchloroformate. The oxazolidinones can be resolved into their optical isomers via chromatography prior to activation, or the unresolved material can be activated directly. The activated oxazolidinone is then acylated to give Compound A by treatment with 3-[4-(4-fluorophenyl)piperidin-1-yl]propylamine.

The following examples are provided to further define the invention without, however, limiting the invention to the particulars of these examples.

EXAMPLE 1

3-[4-(4-Fluorophenyl)piperidin-1-yl]propylamine

Step A. 4-(4-Fluorophenyl)piperidine hydrochloride

To a solution of 4-(4-fluorophenyl)-1,2,3,6-tetrahydropyridine hydrochloride (10 g) in methanol (200 mL) was added 10% palladium on charcoal (0.5 g) and the mixture was hydrogenated at 50 psi for 3 h. The catalyst was removed by filtration and solvent was evaporated to leave the product as a white powder, which was used in the next step without any purification.

M.P. 181–182° C.

$^1$H NMR (CDCl$_3$): δ1.95–2.03 (br d, 2H), 2.14–2.29 (m, 2H), 2.70–2.80 (m, 1H), 2.91–3.07 (br q, 2H), 3.60–3.64 (br d, 2H), 6.96–7.03 (m, 2H), 7.19–7.22 (m, 2H), 9.60 (br s, 1H), 9.71 (br s, 1H).

Step B. 3-[4-(4-Fluorophenyl)piperidin-1-yl] propylphthalimide

A mixture of 4-(4-fluorophenyl)piperidine hydrochloride (5.08 g, 23.2 mmol), 3-bromopropylphthalimide (6.22 g, 23.2 mmol), and potassium carbonate (15 g) in DMF (100 mL) was stirred and heated at 95–100° C. for 12 h. About 80% of the solvent was evaporated at reduced pressure, the residue was diluted with ethyl acetate (200 mL) and washed with brine (3×100 mL) and dried (Na$_2$SO$_4$). Solvent was evaporated and the residue was purified by column chromatography on silica gel using 1/1 hexane-ethyl acetate to 100% ethyl acetate as eluent. This product was crystallized from isopropanol to give a white crystalline solid; m.p. 80–81° C. This material was used in the next step. Concentration of the mother liquor and cooling gave the second crop.

$^1$H NMR (CDCl$_3$): δ1.43–1.52 (m, 2H), 1.67–1.75 (m, 2H), 1.80–1.96 (m, 4H), 2.33–2.46 (m, 3H), 2.94–2.99 (br d, 2H), 3.78 (t, J=7 Hz, 2H), 6.90–7.04 (m, 4H), 7.70–7.74 (m, 2H), 7.84–7.87 (m, 2H).

Step C. 3-[4-(4-Fluorophenyl)piperidin-1-yl] propylamine

To a solution of 3-[4-(4-fluorophenyl)piperidin-1-yl] propylphthalimide (4.5 g, 12.3 mmol) in methanol (200 mL) was added 4 ml of hydrazine and the mixture was refluxed for 8 h. It was cooled, and the white solid was filtered and washed with methanol (20 mL). Solvent was evaporated, and the residue was dried under vacuum for 4 h. Chloroform (50 mL) was added to this material, it was stirred for 1 h and filtered. The white solid was washed with more chloroform (20 mL), and the solvent was evaporated from the combined filtrates to leave the crude product as an oil. It was purified by column chromatography on silica gel using dichloromethane/methanol/2M ammonia in methanol (10/3/1) as the eluent.

$^1$H NMR (CDCl$_3$): δ1.60–1.83 (m, 6H), 1.96–2.07 (m, 4H), 2.40–2.55 (m, 3H), 2.70–2.85 (br t, 2H), 3.03–3.07 (br d, 2H), 6.93–7.00 (m, 2H), 7.14–7.20 (m, 2H).

EXAMPLE 2

(4S,5S)-4-(3,4-Difluorophenyl)-N-[3-[4-(4-fluorophenyl)-1-piperidinyl]propyl]-5-methyl-2-oxo-3-oxazolidine carboxamide

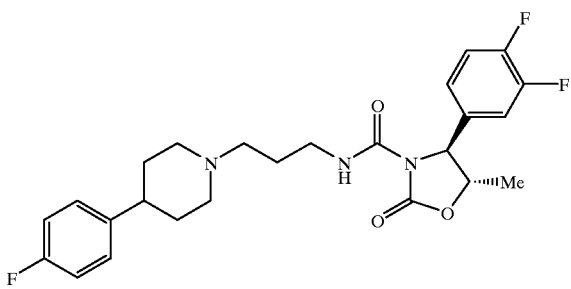

4(S)-(3,4-difluorophenyl)-5(S)-methyloxazolidin-2-one (2 g, 9.4 mmole) was dissolved in THF (20 ml) and cooled to −60° C. for the dropwise addition of n-BuLi (4 ml, 2.5 M in hexane). In a separate flask, p-nitrophenyl chloroformate was dissolved in 20 ml THF and cooled to −60° C. When the addition of n-BuLi was complete, the mixture was aged at −60° C. for 30 minutes. and then transferred via cannula to the p-nitrophenyl chloroformate solution. The reaction mixture was then allowed to warm to room temperature, and reaction progress was monitored by HPLC. After 2.5 hours, 3-(4-(4-fluorophenyl)piperidin-1-yl)propylamine (Example 1) (2.2 g, 9.4 mmole) in THF was added. After 3.5 hours at room temperature age, the solution was diluted with 100 ml water and extracted with 2×50 ml MTBE. The MTBE extractions were combined and washed with 2×50 ml 1M sulfuric acid. The aqueous washes were combined, rendered basic (pH=9–10) with 2 M sodium carbonate, and extracted with 2×100 ml MTBE. The MTBE layers were combined and concentrated, and the title compound was isolated by column chromatography on silica gel using 9:1 EtOAc:MeOH.

EXAMPLE 3

Crystallization of the benzene sulfonic acid salt of (4S,5S)-4-(3,4-Difluorophenyl)-N-[3-[4-(4-fluorophenyl)-1-piperidinyl]propyl]-5-methyl-2-oxo-3-oxazolidine carboxamide (4S,5S)-4-(3,4-Difluorophenyl)-N-[3-[4-(4-fluorophenyl)-1-piperidinyl]propyl]-5-methyl-2-oxo-3-oxazolidine carboxamide (4.75 g, 10 mmoles) and benzenesulfonic acid monohydrate (1.58 g, 10 mmoles) were mixed with ethanol (10 ml) at room temperature and heated to 70° C. to obtain a clear solution. The solution was slowly cooled to about 0° C. with stirring of the solution at room temperature, wherein crystals began to form at about 50° C. The resulting crystals were filtered, washed with ethanol (2×) at 0° C., and then air dried to constant weight to provide the title salt.

The benzene sulfonate salt of L-797,459 was characterized by $^1$H NMR. The $^1$H chemical shifts (in ppm) are listed below. All coupling constants are reported in Hertz (Hz) with proton multiplicities abbreviated as follows: d=doublet, t=triplet, m=multiplet, o=overlapping.

$^1$H NMR (400.25 MHz) δ7.84 (m, 2H), 7.44–7.38 (om, 3H), 7.34–7.27 (om, 2H), 7.23 (m, 2H), 7.16 (m, 1H), 7.03 (m, 2H), 4.98 (d, 5.2, 1H), 4.49 (m, 1H), 3.58 (m, 1H), 3.47 (m, 1H), 3.34 (t, J=6.8, 2H), 3.13–3.00 (om, 4H), 2.85 (tt, J=12.1, 3.8, 1H), 2.05–1.82 (om, 6H), 1.50 (d, J=6.4, 3H).

The salt is characterized by a differential scanning calorimetry (DSC) curve, at a heating rate of 10° C./min in an open cup under flowing nitrogen, exhibiting an endotherm with an extrapolated onset temperature of about 166° C., a peak temperature of about 168° C. and an associated heat of about 83 J/gm. The endotherm is due to melting without decomposition.

The X-ray powder diffraction pattern of the salt is characterized by d-spacings of 19.1, 13.3, 7.16, 6.87, 5.47, 5.05, 4.85, 4.70, 4.42, 4.10, 3.85, 3.62, 3.56, 3.38 and 3.14 Å.

EXAMPLE 4

Preparation of a Capsule for Oral Administration

As a specific embodiment of an oral composition, 53.3 mg of the salt of Example 3 (equivalent to 40 mg of free base) is formulated with sufficient finely divided lactose to provide a total amount of 580 to 590 mg to fill a size O hard gel capsule.

EXAMPLE 5

Screening Assay: Alpha 1a Adrenergic Receptor Binding

Identification of compounds which bind to human alpha 1a adrenergic receptors is done using membranes prepared from the stably transfected human alpha 1a cell line (ATCC CRL 11140). The competition binding reactions (total volume=200 μl) contain 50 mM Tris-HCl pH. 7.4, 5 mM EDTA, 150 mM NaCl, 100 pM [$^{125}$I]-HEAT, membranes which are prepared from the alpha 1a cell line and increasing amounts of unlabeled ligand. Reactions are incubated at room temperature for one hour with shaking. Reactions are filtered onto Whatman GF/C glass fiber filters with a Inotec 96 well cell harvester. Filters are washed three times with ice cold buffer and bound radioactivity is determined (Ki).

EXAMPLE 6

Selective Binding Assays

Identification of compounds which selectively bind to the human alpha 1a adrenergic receptor is done using membranes prepared from stably transfected human alpha 1d and alpha 1b cell lines (ATCC CRL 11138 and CRL 11139, respectively). The competition binding reactions (total volume=200 μl) contain 50 mM Tris-HCl pH. 7.4, 5 mM EDTA, 150 mM NaCl, 100 pM [$^{125}$I]-HEAT, membranes which are prepared from cell lines transfected with the respective alpha 1 subtype expression plasmid and increasing amounts of unlabeled ligand. Reactions are incubated at room temperature for one hour with shaking. Reactions are filtered onto Whatman GF/C glass fiber filters with a Inotec 96 well cell harvester. Filters are washed three times with ice cold buffer and bound radioactivity is determined (Ki).

EXAMPLE 7

Counterscreen: Histamine-1 Selectivity

The binding affinity (Ki in nM) of the compounds of the present invention for histamine H1 receptors can be determined via the binding assay described in Chang et al., *J. Neurochem.* (1979), 32: 1653, or as described in U.S. Pat. No. 5,403,847, or suitable modifications thereof known to those skilled in the art. The assay can be used to eliminate agents which specifically affect binding to hH1 receptors.

EXAMPLE 8

Exemplary Counterscreens

1. Assay Title: Dopamine D2, D3, D4 in Vitro Screen

Objective of the Assay

The objective of this assay is to eliminate agents which specifically affect binding of [3H] spiperone to cells expressing human dopamine receptors D2, D3 or D4.

Method

Modified from VanTol et al, *Nature* (1991), 350: 610–613.

Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 50 mM Tris-HCl pH 7.4 containing EDTA, MgCl[2], KCl, NaCl, CaCl[2] and ascorbate to give a 1 Mg/mL suspension. The assay is initiated by adding 50–75 µg membranes in a total volume of 500 µl containing 0.2 nM [3H]-spiperone. Non-specific binding is defined using 10 µM apomorphine. The assay is terminated after a 2 hour incubation at room temperature by rapid filtration over GF/B filters presoaked in 0.3% PEI, using 50 mM Tris-HCl pH 7.4.

2. Assay Title: Serotonin 5HT1a

Objective of the Assay

The objective of this assay is to eliminate agents which specifically affect binding to cloned human 5HT1a receptor Method Modified from Schelegel and Peroutka, *Biochemical Pharmacology* (1986), 35: 1943–1949.

Mammalian cells expressing cloned human 5HT1a receptors are lysed in ice-cold 5 mM Tris-HCl, 2 mM EDTA (pH 7.4) and homogenized with a polytron homogenizer. The homogenate is centrifuiged at 1000×g for 30', and then the supernatant is centrifuged again at 38,000×g for 30'. The binding assay contains 0.25 nM [3H]8-OH-DPAT (8-hydroxy-2-dipropylamino-1,2,3,4-tetrahydronaphthalene) in 50 mM Tris-HCl, 4 mM CaCl2 and 1 mg/ml ascorbate. Non-specific binding is defined using 10 µM propranolol. The assay is terminated after a 1 hour incubation at room temperature by rapid filtration over GF/Cfilters

EXAMPLE 9

Exemplary Functional Assays

In order to confirm the specificity of compounds for the human alpha 1a adrenergic receptor and to define the biological activity of the compounds, the following functional tests may be performed:

1. In vitro Rat, Dog and Human Prostate and Dog Urethra

Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $CO_2$/95% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 µM (for rat), 10 µM (for dog) and 20 µM (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

$EC_{50}$ values are calculated for each group using GraphPad Inplot software. $pA_2$ (-log $K_b$) values were obtained from Schild plot when three or more concentrations were tested. When less than three concentrations of antagonist are tested, $K_b$ values are calculated according to the following formula $K_b$=[B], where x is the ratio of $EC_{50}$ of agonist in the presence and absence of antagonist and [B] is the antagonist concentration.

2. Measurement of Intra-Urethral Pressure in Anesthetized Dogs

PURPOSE: Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because we have identified the alpha 1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha 1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS: Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha 1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four paramenter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A crystalline pharmaceutically acceptable salt, which is the benzenesulfonic acid salt of Compound A of formula:

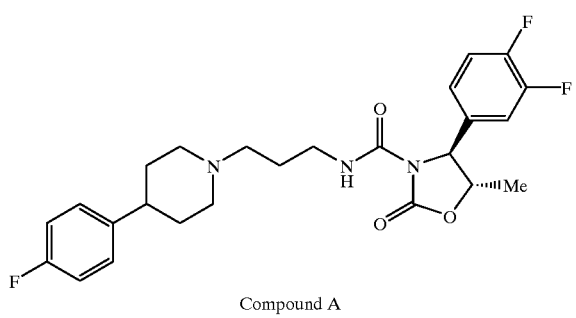

Compound A or a solvate thereof.

2. The crystalline salt of claim 1, which is a salt of formula:

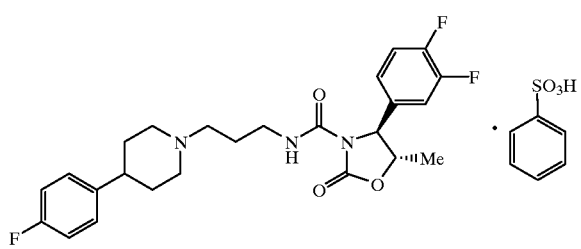

or a solvate thereof.

3. The crystalline salt of claim 2 characterized by a differential scanning calorimetry (DSC) curve at a heating rate of 10° C./min in an open cup under flowing nitrogen, exhibiting an endotherm with an extrapolated onset temperature of about 166° C., a peak temperature of about 168° C. and an associated heat of about 83 J/gm.

4. The crystalline salt of claim 2 characterized by an x-ray powder diffraction pattern having d-spacings of 19.1, 13.3, 7.16, 6.87, 5.47, 5.05, 4.85, 4.70, 4.42, 4.10, 3.85, 3.62, 3.56, 3.38 and 3.14 Å.

5. A pharmaceutical composition comprising the crystalline salt of claim 1 and a pharmaceutically acceptable carrier.

6. A pharmaceutical composition made by combining a crystalline salt of claim 1 and a pharmaceutically acceptable carrier.

7. A process for making a pharmaceutical composition comprising combining a crystalline salt of claim 1 and a pharmaceutically acceptable carrier.

8. A method of treating benign prostatic hyperplasia in a subject in need thereof which comprises administering to the subject a therapeutically effective amount of the crystalline salt of claim 1.

9. A method of relaxing lower urinary tract tissue in a subject in need thereof which comprises administering to the subject a therapeutically effective amount of the crystalline salt of claim 1.

10. A method of treating benign prostatic hyperplasia in a subject in need thereof which comprises administering to the subject a therapeutically effective amount of the pharmaceutical composition of claim 5.

11. A method of relaxing lower urinary tract tissue in a subject in need thereof which comprises administering to the subject a therapeutically effective amount of the pharmaceutical composition of claim 5.

12. A process for making a crystalline pharmaceutically acceptable benzensulfonic acid salt of Compound A of formula:

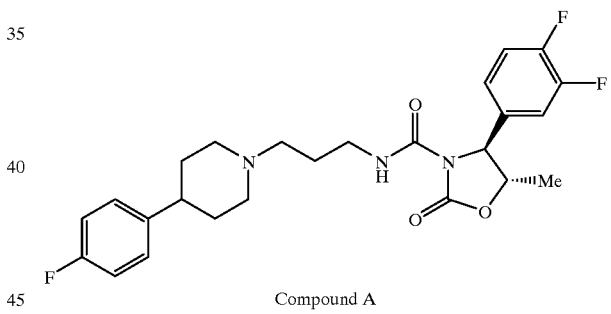

Compound A or a solvate thereof, which comprises:
(a) dissolving Compound A and benzensulfonic acid in a solvent to form a solution; and
(b) treating the solution of step (a) to form the crystalline salt.

13. The process of claim 12, wherein at least about one mole equivalent of benzenesulfonic acid is dissolved in the solution per mole equivalent of Compound A.

14. The process of claim 12, wherein dissolution step (a) comprises mixing Compound A in the solvent with the benzenesulfonic acid and then heating the mixture to form the solution.

15. The process of claim 14, wherein treatment step (b) comprises cooling the heated solution to form the crystalline salt.

16. The process of claim 12, wherein the solvent is selected from methanol, ethanol, 2-propanol, ethyl acetate, isopropyl acetate, butanol, hexanes, toluene, ethyl ether, or a mixture thereof.

17. The process of claim 16, wherein the solvent is ethanol.

18. The process of claim 12, wherein the salt is of formula:

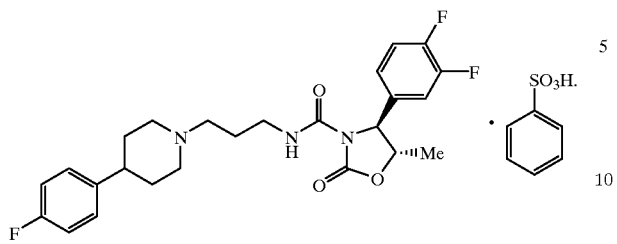

19. A process for forming a crystalline salt of formula:

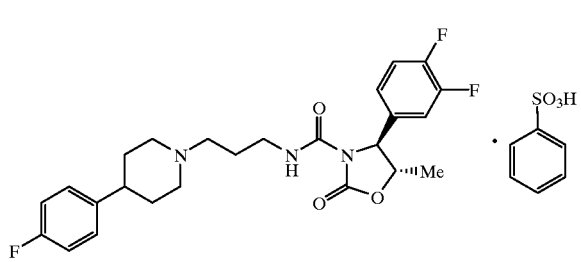

or a solvate thereof, which comprises:

(a) heating a mixture of Compound A and benzensulfonic acid in ethanol to form a solution, wherein the mixture contains at least about one mole equivalent of benzensulfonic acid per mole equivalent of Compound A; and (b) cooling the solution to form the crystalline salt.

20. A crystalline pharmaceutically acceptable salt of benzenesulfonic acid, or a solvate thereof, made by dissolving a free base compound of formula:

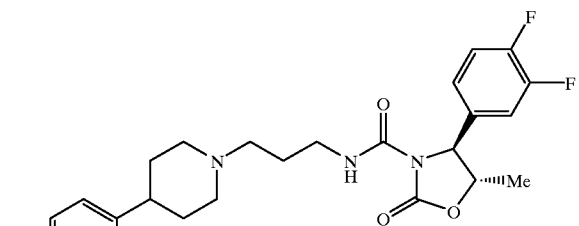

and benzenesulfonic acid in a solvent to form a solution; and treating the solution to form the crystalline salt.

* * * * *